US00PP36870P2

(12) United States Plant Patent
Slowinski

(10) Patent No.: US PP36,870 P2
(45) Date of Patent: Jul. 29, 2025

(54) ***MISCANTHUS* PLANT NAMED 'Lady in Red'**

(50) Latin Name: *Miscanthus sinensis*
Varietal Denomination: Lady in Red

(71) Applicant: Krzysztof Slowinski, Ladek (PL)

(72) Inventor: Krzysztof Slowinski, Ladek (PL)

( * ) Notice: Subject to any disclaimer, the term of this patent is extended or adjusted under 35 U.S.C. 154(b) by 0 days.

(21) Appl. No.: 18/951,034

(22) Filed: Nov. 18, 2024

(51) Int. Cl.
*A01H 6/00* (2018.01)
*A01H 5/02* (2018.01)

(52) U.S. Cl.
USPC ..... Plt./384

(58) Field of Classification Search
USPC ..... Plt./384
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Miscanthus* plant named 'Lady in Red' is disclosed, characterized by spectacular red foliage in autumn. Red autumn leaves contrast beautifully with silvery-white flower panicles. Plants are low-maintenance and winter-hardy. The new variety is a *Miscanthus*, typically produced as an outdoor ornamental plant.

3 Drawing Sheets

Latin name of the genus and species: *Miscanthus sinensis*.
Variety denomination: 'Lady in Red'.

BACKGROUND OF THE INVENTION

The new cultivar was discovered by the inventor in summer of 2013 in a field of *Miscanthus* seedlings in Ladek, Poland. The seed parent is the variety *Miscanthus* 'Veitshochheim', unpatented. The pollen parent is unknown.

Asexual reproduction of the new cultivar 'Lady in Red' was first performed in Ladek, Poland by vegetative division in 2013. Subsequently, at least 6 generations of 'Lady in Red' have been reproduced and have shown that the unique features of this cultivar are stable and reproduced true to type.

The inventor has filed an application with the CPVO Oct. 16, 2020, having application number 2020/2557. This application was Granted Jun. 15, 2023, grant number 63250. The first sale of the new cultivar occurred during July of 2024 in Poland, directly by the inventor to a customer of the inventor. These disclosures fall within the exception allowed under 102(b)(1).

SUMMARY OF THE INVENTION

The cultivar 'Lady in Red' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Lady in Red'. These characteristics in combination distinguish 'Lady in Red' as a new and distinct *Miscanthus* cultivar:

1. Spectacular bright red autumn color.
2. Neat growth habit.
3. Beautiful contrast between the red leaves and silvery white flower panicles.
4. Low maintenance, winter hardy.

PARENT COMPARISONS

Plants of the new cultivar 'Lady in Red' are similar to plants of the seed parent variety in most horticultural characteristics, however, 'Lady in Red' differs in the following:

1. Plants of the new variety are faster growing than plants of the seed parent.
2. Plants of the new variety are taller than plants of the seed parent.
3. Foliage color of the new variety is dark purple and green to bright red, while the foliage color of the seed parent is yellow.

The pollen parent cannot be identified with certainty.

COMMERCIAL COMPARISONS

Plants of the new cultivar 'Lady in Red' can be compared to the commercial variety *Miscanthus sinensis* 'Dronning Ingrid', unpatented. Plants of the new cultivar 'Lady in Red' are similar to plants of 'Dronning Ingrid' in most horticultural characteristics, however, 'Lady in Red' differs in the following:

1. Foliage color of the new variety is red for 2 months, while the foliage color of this comparator is red for a shorter time.
2. Plants of the new variety stay upright, while plants of this comparator are very floppy and easily fall over.

Plants of the new cultivar 'Lady in Red' can be compared to the commercial variety *Miscanthus* 'Ballerina', unpatented. Plants of the new cultivar 'Lady in Red' are similar to plants of 'Ballerina' in most horticultural characteristics; however, 'Lady in Red' differs in the following:

1. Foliage color of the new variety is dark purple and green to bright red, while the foliage color of this comparator is green, orange, and yellow.
2. Plants of the new variety are shorter than plants of this comparator.

BRIEF DESCRIPTION OF THE PHOTOGRAPHS

The accompanying photograph in FIG. 1 illustrates in full color a typical plant of 'Lady in Red' grown outdoors in Ladek, Poland, photographed in October with the darkest red foliage. This plant is approximately 3-years old, shown growing in the ground.

Figure 1:
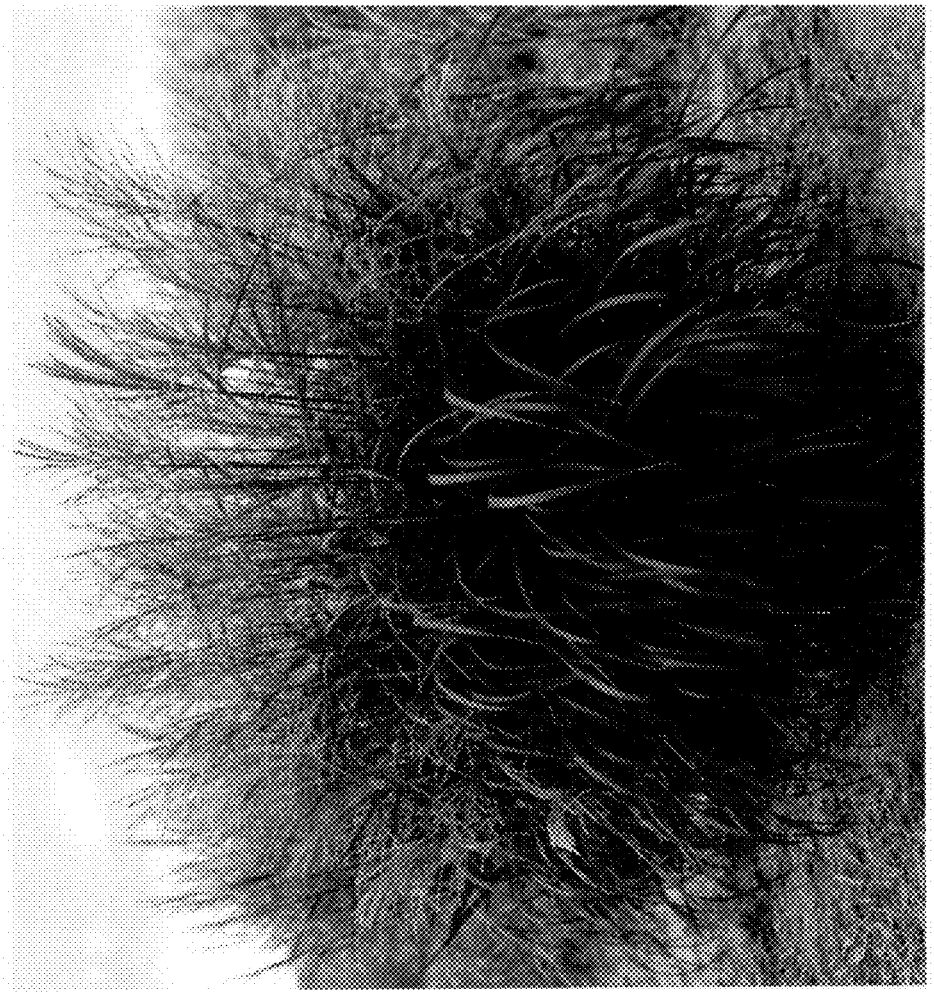
Figure 2:
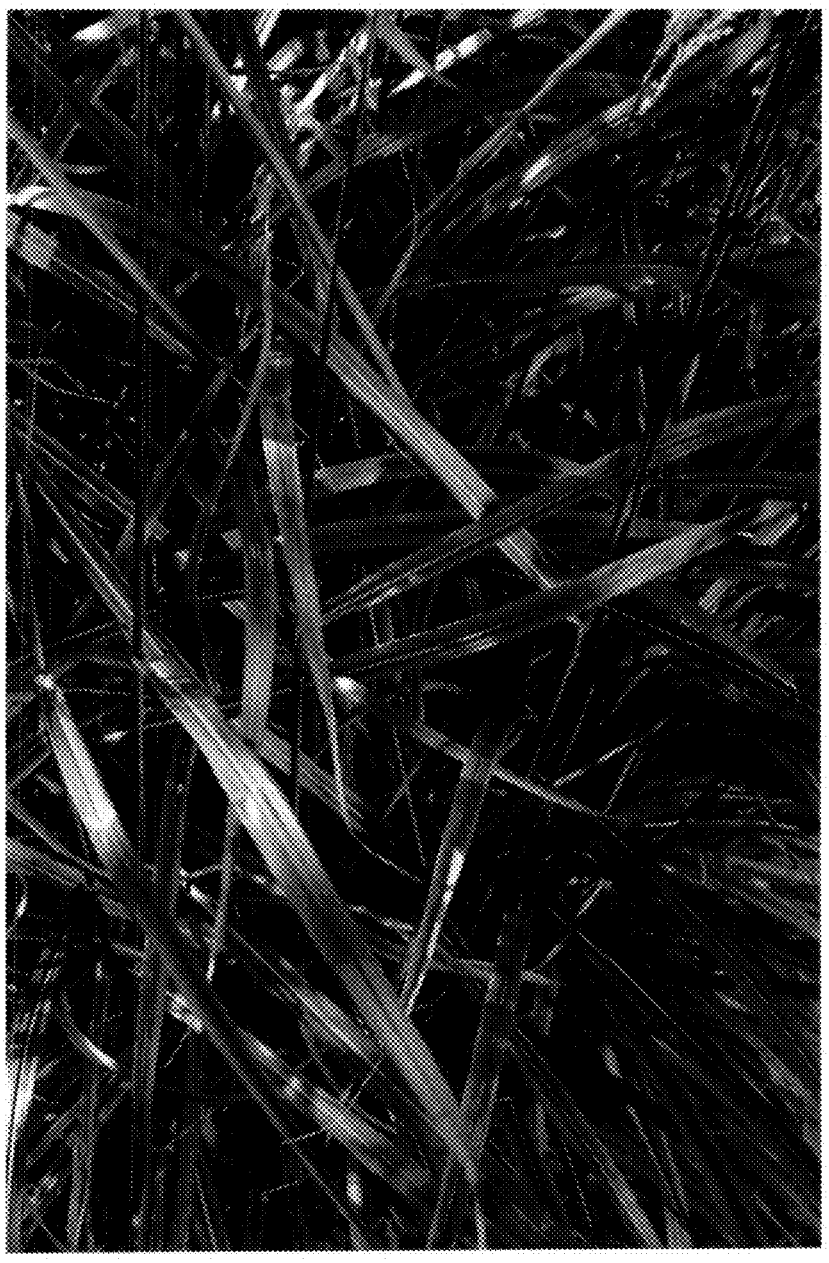
FIG. 2 is a close-up view of the foliage of this plant, also photographed in October.
Figure 3:
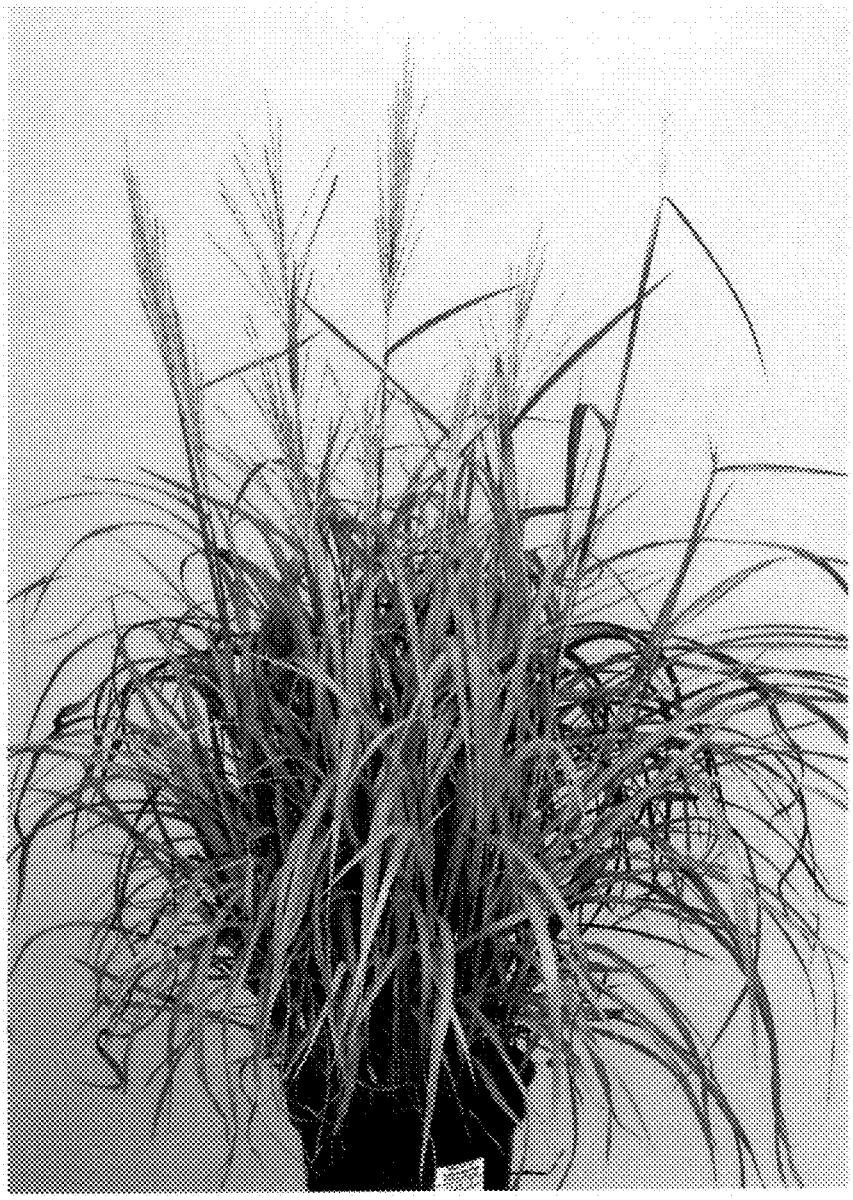
FIG. 3 is plant of the new cultivar in a 25 cm pot at around 9 months old, photographed in early August in Boskoop, the Netherlands as foliage is just beginning to change color.

The photographs were taken using conventional techniques and although colors may appear different from actual colors due to light reflectance they are as accurate as possible by conventional photographic techniques.

DETAILED BOTANICAL DESCRIPTION

In the following description, color references are made to The Royal Horticultural Society Colour Chart 6$^{th}$ edition 2015, except where general terms of ordinary dictionary significance are used. The following observations and measurements describe 'Lady in Red' plants grown outdoors Boskoop, the Netherlands. Plants were approximately 1 year old. Temperatures ranged from 8° C. to 20° C. at night to 16° C. to 30° C. during the day. No artificial light, photoperiodic treatments or chemical treatments were given to the plants. Measurements and numerical values represent averages of typical plant types.

Botanical classification: *Miscanthus sinensis* 'Lady in Red.'.

PLANT

Plant type: Perennial ornamental grass.
Growth habit: Broad upright.
Plant shape: Broad oblong to obovate.
Height: Average 63 cm to top of foliar plane; 87.2 cm to top of floral plane.
Plant spread: Average 78.8 cm.
Growth rate: Moderate.
Vigor: Moderate.
Branching characteristics: Main shoots grow from the base, no lateral branching. No pinching required.
Number of shoots per plant: Average 82 basal shoots.
Average length of shoot: 60.5 cm (measured from base of shoot to base of inflorescence).
Average width of shoot: 0.4 cm.
Internode length: Average 8.4 cm (varying between 1.5 cm and 21.5 cm).
Stem:
- *Shape*.—Rounded.
- *Strength*.—Strong.
- *Luster*.—Moderately glossy.
- *Aspect*.—Average 10°.
- *Color*.—Developing: RHS Yellow-Green 144C. Mature: RHS Yellow-Green 144B. At internodes: RHS Yellow-Green 144B, finely mottled White N155A just below internode.
- *Pubescence*.—A ring of adpressed short hairs is present at nodes, average length: 2.0 mm, colored RHS Greyed-White 156D.

Root structures: None.

FOLIAGE

Leaf:
- *Arrangement*.—Alternate.
- *Compound or single*.—Single.
- *Quantity of leaves per shoot*.—Average 8.
- *Length*.—Average 37.7 cm, excluding sheath.
- *Width*.—Approximately 1.1 cm.
- *Apex*.—Narrow and long acuminate.
- *Base*.—Sheathing.
- *Sheath length*.—Average 12.4 cm.
- *Sheath width*.—Average 0.45 cm.
- *Sheath color*.—RHS Yellow-Green 146C, moderately to strongly tinged Greyed-Red 182B.
- *Shape of blade*.—Linear.
- *Aspect*.—Very slightly carinate, tips twisted, leaves arching.
- *Margin*.—Smooth, but very sharp when rubbed downwards; due to very small, very sharp teeth, too small to be measured with R.H.S. chart.
- *Texture of top surface*.—Glabrous, smooth.
- *Texture of bottom surface*.—Glabrous, smooth.
- *Pubescence*.—Ligules moderately pubescent with thin hairs, average length: 0.3 cm, colored close to RHS White N155A.
- *Rugosity*.—Both sides non-rugose.
- *Luster, upper side*.—Slightly glossy.
- *Luster, under side*.—Matte.
- *Color*.—Young foliage upper side: RHS Yellow-Green 143B. Young foliage under side: RHS Yellow-Green 143A. Mature foliage upper side: Blend of RHS Yellow-Green 143A and 146B. Mature foliage under side: RHS Green 137C and 137D. Autumn color, upper side: Beginning to turn RHS Greyed-Red 178B, starting early August to September. In October the darkest red color appears; Greyed-Purple 184A flushed Red 53A with a center streak around central vein colored Greyed-Purple 187A. Autumn color, under side: Beginning to turn RHS Greyed-Red 173B, starting early August to September. In October the darkest red color appears, Greyed-Red 181A flushed Red 53C with a center streak around central vein colored Yellow-Green 146A.
- *Venation*.—Type: Parallel, only main vein distinguishable from rest of leaf blade. Color, upper side: RHS White N155A. Color, under side: RHS Green 137D.

Petiole: Not present, leaves sheathing.

INFLORESCENCE

Inflorescence:
- *Type and form*.—Panicle.
- *Height*.—Average 21.2 cm.
- *Diameter*.—Average 6.1 cm.
- *Quantity of flowers per inflorescence*.—Average 500.
- *Quantity of flowers per plant*.—Average 5,000.
- *Quantity of flower buds per plant*.—Average 2,000.
- *Quantity of flowers and flower buds per plant*.—Average 7,000.
- *Natural flowering season*.—Late summer.
- *Lastingness of the inflorescence*.—About 3 months.
- *Time to flower or response time*.—Average 10 months.

Flower bud:
- *Length*.—Average 0.6 cm.
- *Diameter*.—Average 0.15 cm.
- *Shape*.—Narrow ovate.
- *Texture*.—Smooth, glabrous, covered by fine hairs extending from the base of the floret.
- *Luster*.—Moderately glossy.
- *Color*.—RHS Grey-Brown 199C, hairs colored transparent White NN155D.

Flower:

*Type and form*.—Single, flowers consisting of two glumes, one palea and one awned lemma.

*Aspect*.—Upright.

*Flowering habit*.—Very freely.

*Fragrance*.—None.

*Shape*.—Single.

*Height*.—Average 0.5 cm.

*Diameter*.—Average 0.5 cm.

*Length*.—Average 0.7 cm.

*Longevity on plant*.—Average one month.

*Persistence*.—Persistent.

Petals:

*Type or form*.—Flowers consisting of two glumes, one palea and one awned lemma. Two glumes oppositely placed at the base of each individual flower, lemma and palea oppositely, alternately placed above the glumes.

*Texture*.—Glumes, lemma and palea glabrous, very slightly glossy.

*Shape*.—Glumes, lemma and palea ovate, strongly concave.

*Margin*.—Glumes, lemma and palea entire.

*Base*.—Glumes, lemma and palea cuneate.

*Apex*.—Glumes, lemma and palea narrow acute.

*Length*.—Glumes: 0.5 cm. Palea: 0.3 cm. Lemma: 0.7 cm.

*Width*.—Glumes: 0.75 mm. Palea: 0.75 mm. Lemma: 0.5 mm.

*Color*.—When opening and at maturity, both sides: Glumes and lemma colored RHS Greyed-Orange 165B to 165C; awn colored Greyed-Orange 177D; palea colored transparent RHS Greyed-White 156D.

*Venation*.—No venation visible; glumes, palea and lemma not fading.

*Pubescence*.—One whorl of fine hairs extending from the base of the floret, average length: 0.6 cm, colored RHS Greyed-White 156D.

Calyx/sepals: No separate calyx and corolla visible.

Peduncles:

*Terminal length*.—Average 32.1 cm.

*Terminal diameter*.—Average 1.75 mm.

*Angle to lateral branch axis*.—Average 0° (=straight on top of stem).

*Strength*.—Moderately strong.

*Texture*.—Smooth, glabrous.

*Luster*.—Slightly glossy.

*Color*.—RHS Yellow-Green 144B.

Pedicels:

*Length*.—Average 3.0 mm.

*Diameter*.—Average 0.5 mm.

*Angle to peduncle axis*.—Average 5°.

*Strength*.—Moderately strong.

*Texture*.—Smooth, glabrous.

*Luster*.—Moderately glossy.

*Color*.—RHS Yellow-Green 151D.

REPRODUCTIVE ORGANS

Stamens:

*Number*.—Average 2.

*Filament length*.—Average 0.1 cm.

*Filament color*.—Transparent RHS White NN155D.

Anther:

*Shape*.—Narrow oblong.

*Length*.—Average 1.5 mm.

*Width*.—Average 0.5 mm.

*Color*.—RHS Grey-Brown N199D.

*Pollen*.—None.

*Pistil*.—Number: Average 2. Length: Average 0.2 cm.

*Stigma*.—Shape: Feather-like. Length: Average 0.1 cm. Diameter: Average 0.3 mm. Color: RHS Brown 200A to 200B.

*Style*.—Length: Average: 0.1 cm. Color: Transparent RHS White NN155D. Ovary color: RHS Yellow-Green 144B.

OTHER CHARACTERISTICS

Fruit and seed: Not observed.

Disease resistance: Similar resistance and susceptibility to pests and diseases of other *Miscanthus sinensis* varieties. *Miscanthus* are not prone to pest problems, however pests which can be found on *Miscanthus* include *Miscanthus* mealybug (*Miscanthiococcus miscanthi*) and *Duplachionaspis divergens*. Diseases are typically not common, however *Miscanthus* blight (*Leptosphaeria anamorph stagnospora*) can affect plants. *Colletotrichum* (anthracnose) can also affect *Miscanthus sinensis*.

Temperature tolerance: Observed to tolerate temperatures from −17° C. to 40° C. USDA zone 6 to zone 10.

Rain/wind tolerance: Moderate to high tolerance to rain. Very high tolerance to wind.

What is claimed is:

1. A new and distinct cultivar of *Miscanthus* plant named 'Lady in Red' as herein illustrated and described.

* * * * *